US 8,878,130 B2

(12) United States Patent
Inada et al.

(10) Patent No.: US 8,878,130 B2
(45) Date of Patent: Nov. 4, 2014

(54) SCANNING ELECTRON MICROSCOPE AND SCANNING TRANSMISSION ELECTRON MICROSCOPE

(75) Inventors: Hiromi Inada, Tokyo (JP); Kuniyasu Nakamura, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/232,526

(22) PCT Filed: Jul. 19, 2012

(86) PCT No.: PCT/JP2012/068369
§ 371 (c)(1),
(2), (4) Date: Jan. 13, 2014

(87) PCT Pub. No.: WO2013/012041
PCT Pub. Date: Jan. 24, 2013

(65) Prior Publication Data
US 2014/0138542 A1  May 22, 2014

(30) Foreign Application Priority Data
Jul. 20, 2011 (JP) .................................. 2011-158548

(51) Int. Cl.
*H01J 37/26* (2006.01)
*H01J 37/28* (2006.01)
(Continued)

(52) U.S. Cl.
CPC ............... *H01J 37/21* (2013.01); *H01J 37/244* (2013.01); *H01J 2237/1532* (2013.01); *H01J 37/153* (2013.01); *H01J 2237/2611* (2013.01);
(Continued)

(58) Field of Classification Search
CPC . H01J 37/21; H01J 2237/21; H01J 2237/221; H01J 37/222; H01J 37/04; H01J 2237/226; H01J 37/244; H01J 2237/0455; H01J 2237/0492; H01J 2237/1532; H01J 2237/2448; H01J 2237/2802
USPC .................................. 250/306, 307, 310, 311
See application file for complete search history.

(56) References Cited

U.S. PATENT DOCUMENTS
6,538,249 B1 * 3/2003 Yoshida et al. ................... 850/9
7,521,675 B2 * 4/2009 Kawasaki et al. ............. 250/310
(Continued)

FOREIGN PATENT DOCUMENTS
EP 0 566 963 A2 10/1993
JP 05-299048 A 11/1993
(Continued)

OTHER PUBLICATIONS
International Search Report, w/ English translation thereof, issued in International Application No. PCT/JP2012/068369 dated Sep. 11, 2012.
(Continued)

Primary Examiner — Michael Logie
(74) Attorney, Agent, or Firm — McDermott Will & Emery LLP

(57) ABSTRACT

A scanning transmission electron microscope according to the present invention includes an electron lens system having a small spherical aberration coefficient for enabling three-dimensional observation of a 0.1 nm atomic size structure. The scanning transmission electron microscope according to the present invention also includes an aperture capable of changing an illumination angle; an illumination electron lens system capable of changing the probe size of an electron beam probe and the illumination angle; a secondary electron detector (9); a transmission electron detector (13); a forward scattered electron beam detector (12); a focusing unit (16); an image processor for identifying image contrast; an image processor for computing image sharpness; a processor for three-dimensional reconstruction of an image; and a mixer (18) for mixing a secondary electron signal and a specimen forward scattered electron signal.

12 Claims, 15 Drawing Sheets

(51) Int. Cl.
*H01J 37/244* (2006.01)
*H01J 37/153* (2006.01)
*H01J 37/21* (2006.01)
*G01N 23/22* (2006.01)

(52) U.S. Cl.
CPC ........ *H01J 2237/21* (2013.01); *H01J 2237/221* (2013.01); *H01J 37/28* (2013.01); *H01J 2237/24475* (2013.01); *H01J 2237/226* (2013.01); *H01J 37/263* (2013.01); *H01J 2237/153* (2013.01); *H01J 2237/0492* (2013.01); *G01N 23/2206* (2013.01); *H01J 2237/2802* (2013.01); *H01J 2237/0455* (2013.01); *H01J 2237/2448* (2013.01); *H01J 2237/225* (2013.01)
USPC ............ 250/310; 250/306; 250/307; 250/311

(56) References Cited

U.S. PATENT DOCUMENTS

| | | | |
|---|---|---|---|
| 7,888,640 B2* | 2/2011 | Tachibana et al. | 250/310 |
| 8,222,601 B2* | 7/2012 | Tachibana et al. | 250/310 |
| 8,405,026 B2* | 3/2013 | Shojo et al. | 250/311 |
| 2004/0188611 A1 | 9/2004 | Takeuchi et al. | |
| 2005/0072920 A1 | 4/2005 | Inada | |
| 2005/0161601 A1 | 7/2005 | Kochi et al. | |
| 2006/0226362 A1* | 10/2006 | Kitsuki et al. | 250/310 |
| 2007/0289953 A1* | 12/2007 | Furuta et al. | 219/121.2 |
| 2010/0059676 A1* | 3/2010 | Shojo et al. | 250/311 |
| 2011/0095184 A1* | 4/2011 | Tachibana et al. | 250/311 |
| 2014/0138542 A1* | 5/2014 | Inada et al. | 250/310 |

FOREIGN PATENT DOCUMENTS

| | | |
|---|---|---|
| JP | 2004-214060 A | 7/2004 |
| JP | 2005-108567 A | 4/2005 |
| JP | 2006-003235 A | 1/2006 |
| JP | 2006-049161 A | 2/2006 |
| JP | 2008-084643 A | 4/2008 |
| JP | 2008-139085 A | 6/2008 |
| JP | 2008-270056 A | 11/2008 |
| JP | 2011-022059 A | 2/2011 |

OTHER PUBLICATIONS

Y. Zhu et al., "Imaging single atoms using secondary electrons with an aberration-corrected electron microscope," Letters Published Online: Sep. 20, 2009; Nature Materials, vol. 8, Oct. 2009, pp. 808-812.

Hoyden, R. et al: "Extended Depth of Field for High-Resolution Scanning Transmission Electron Microscopy", Microscopy and Microanalysis 17, 2011, pp. 75-80.

Inada, H., et al: "High Resolution Secondary-Electron and ADF-STEM Imaging with Hitachi HD2700C Scanning Transmission Electron Microscope", Microscopy and Microanalysis, 16, 2010, pp. 102-103.

Van den Broek, W., et al.: "A model based reconstruction technique for depth sectioning with scanning transmission electron microscopy", Ultramicroscopy, 110, 2010, pp. 548-554.

Xin, H.L., et al: "Aberration-corrected ADF-STEM depth sectioning and prospects for reliable 3D imaging in S/TEM", Journal of electron microscopy, 58, 2009, pp. 157-165.

German Office Action issued in corresponding German Application No. 112012002668.3, dated Feb. 17, 2014, with English translation.

* cited by examiner

| (m,n) | Δf0 | Δf1 | Δf2 | ... |
|---|---|---|---|---|
| (0,0) | S1 | S2 | S3 | S4 |
| (0,1) | S1 | Image sharpness evaluation value table | | |
| (0,2) | S2 | | | |
| ... | | | | |

Secondary electron image

FIG. 18

| (m,n) | $Z_{DOF}$ | $\alpha$ | C1 | C2 | C3 |
|---|---|---|---|---|---|
| (0,0) | $Z_{DOF1}$ | $\alpha 1$ | IC1-1 | IC2-1 | IC3-1 |
| (0,1) | $Z_{DOF1}$ | $\alpha 1$ | IC1-1 | IC2-1 | IC3-1 |
| (0,2) | $Z_{DOF2}$ | $\alpha 2$ | IC1-2 | IC2-2 | IC3-2 |
| ... | ... | ... | ... | ... | ... |

Table of pixel-by-pixel optimum focal depth, illumination angle, and condensing lens current

SCANNING ELECTRON MICROSCOPE AND SCANNING TRANSMISSION ELECTRON MICROSCOPE

RELATED APPLICATIONS

This application is the U.S. National Phase under 35 U.S.C. §371 of International Application No. PCT/JP2012/068369, filed on Jul. 19, 2012, which in turn claims the benefit of Japanese Application No. 2011-158548, filed on Jul. 20, 2011, the disclosures of which Applications are incorporated by reference herein.

TECHNICAL FIELD

The present invention relates to a scanning transmission electron microscope, particularly to a charged particle instrument for forming a three-dimensional image based on a specimen secondary electron scanning image having an atomic resolution and a specimen transmitted electron image, a scanning transmission electron microscope for visualizing an internal structure of a specimen when the observed specimen has different internal structures or compositions, and a scanning transmission electron microscope for element identification based on a combination of a specimen secondary electron scanning image and a scanned specimen magnified image by forward scattered electrons.

BACKGROUND ART

In a scanning electron microscope or a scanning transmission electron microscope that scans a specimen with an electron beam to obtain a magnified image of the specimen, various kinds of electrons are obtained due to the interaction between the specimen and the irradiation primary electron beam, such as secondary electrons, backscattered electrons (specimen backscattered electrons), specimen forward scattered electrons, and transmission electrons. Depending on the relationship between the specimen and the detection position, the various kinds of electrons are discriminated when detected, and characteristic image contrasts are obtained by respective detectors, whereby a scanning magnified image of the specimen can be formed.

With reference to the scanning transmission electron microscope as an example, three-dimensional specimen information obtained from the specimen image and resolution will be described.

The scanning transmission electron microscope forms an image based on secondary electrons, forward scattered electrons, or transmission electrons that are produced from the specimen when scanned with a minute spot of an electron beam, and has a subnanometer-size attainable resolution.

(i-1) Image Resolution of Forward Scattered Electron Image and Transmission Electron Image.

With the specimen forward scattered electrons, when the scattering angle acquisition angle is large, a contrast referred to as "Z-contrast", which is proportional to the square of the atomic number Z of the specimen, can be obtained. This image is due to Rutherford scattering by the atomic nucleus, and is indicated by the convolution of the size of the incident electron beam and the size of the specimen atoms. Thus, image resolution is determined in accordance with the spot size of the incident electron beam.

Transmission electrons consist of electrons that have passed through the specimen and electrons that have lost energy slightly due to inelastic scattering, and form an image similar to an image by the so-called transmission electron microscope. The transmission electron image is separated into amplitude contrast and phase contrast, and an image of atomic resolution is formed by the phase contrast formed by an interference electron beam from the specimen. In the image of atomic resolution by transmission electrons, it is not easy to identify the position of atoms because the contrast formed by the electron beam focused on the specimen is varied. Normally, interpretation based on a comparison with a simulation image is required.

(i-2) Three-Dimensional Information of Forward Scattered Electron Image and Transmission Electron Image Image formation by specimen forward scattered electrons and transmission electrons provide only planar information. When the specimen has a thickness in the depth direction, because the signal image is due to electrons that have passed through the specimen or to forward scattered electrons, structures or portions of different compositions that exist in the depth direction with respect to the electron beam incident direction are superposed. As a result, there has been the problem that unwanted signals are occasionally observed.

The above characteristics will be described with reference to a specific example. When catalyst particles with a diameter on the order of several to several tens of nanometers are to be observed and analyzed by using the scanning transmission electron microscope, it is necessary to find a field of view in which the support material for the catalyst particles for observation or other catalyst particles do not exist on the axis of observation in a superposed manner. However, in the case of the electron microscope only provided with a forward scattered electron or transmission electron detector, as described above, the observed image is an image that has substantially completely transmitted through the specimen. As a result, the depth direction position cannot be identified, and the field of view is difficult to find. Further, in the image formed by forward scattered or transmission electrons, the image information is two-dimensional and planar, which is not suitable for stereoscopic structure observation in an atomic size.

With reference to FIG. 2, the difference in focal depth between a secondary electron image and a specimen forward scattered electron image will be described. FIG. 2 schematically shows the different ways in which an observed two-dimensional image is viewed. Suppose a state such that specimen structures are perpendicularly arranged with respect to the incident primary electron beam. Then, in a secondary electron image (SE image) and a specimen forward scattered electron image (DF-STEM image), images reflecting the specimen structure are observed as shown. When the specimen structure is not more than several nm or like an atomic arrangement, giving a focusing shift of the irradiation electron beam (defocus $\Delta f$) of approximately 20 nm almost eliminates the contrast reflecting the structures in the case of the secondary electron image, while enabling observation with a strong contrast maintained in the case of the specimen forward scattered electron image.

Namely, in the case of image formation by transmission electrons or specimen forward scattered electrons, signals from structures that exist in the specimen depth direction are all projected, so that the stereoscopic structure of the specimen cannot be grasped, nor can the internal structures of the specimen be clearly separated.

(ii-1) Image Resolution of Secondary Electron Image

Image resolution in a secondary electron image is a composition of the two events of electron beam probe size and electron diffusion in specimen.

The probe size of the electron beam is given by expression 1, or the so-called Everhart's formula:

[Expression 1]

$$d = \sqrt{\left(\frac{1}{4}C_s\alpha^3\right)^2 + \left(\frac{1}{2}C_c\left(\frac{\delta E}{E}\right)\alpha\right)^2 + \left(\frac{0.61\lambda}{\alpha}\right)^2 + \frac{4i_p}{\beta\pi^2\alpha^2}}$$ Expression 1

The probe size of the primary electron beam according to expression 1 is given by the electron microscope device factors, and ideally provides the image resolution of the scanning electron microscope. The first term is the influence of spherical aberration ($C_s$) of the electron lens and proportional to the cube of the electron beam illumination angle α. The second term is the effect of chromatic aberration ($C_c$) of the electron lens, and dependent on the amount of minute displacement δE of the acceleration voltage E of the primary electron beam and the illumination angle α. The third term is the diffraction aberration. The fourth term is dependent on the function of brightness β of the electron source and electron beam probe current $i_p$.

FIG. 8 shows the relationship between the electron beam illumination angle and the electron beam probe size, showing the relationship between the electron beam probe size and the illumination angle according to expression 1. In a charged particle instrument according to the present invention, when an aberration corrector for correcting the spherical aberration $C_s$ of the electron beam probe is installed, the first term of expression 1 can be made substantially zero. By using an electron microscope of the scanning electron microscope equipped with the spherical aberration corrector, an electron beam probe of not more than 0.1 nm can be formed. The electron beam probe size becomes smaller as the illumination angle is increased according to the terms following the second term. The minimum value is given by the illumination angle $\alpha_0$, from which the probe size becomes greater as the illumination angle is increased. Namely, the image resolution of the obtained scanning magnified image is increased, enabling the observation of smaller structures.

Next, the electron diffusion in specimen will be described. For example, when a secondary electron image of a specimen is to be obtained by using a general-purpose scanning electron microscope with acceleration voltage set lower than 30 kV, the primary electron beam causes multiple scattering in the specimen and has a teardrop-shaped divergence. Thus, secondary electrons are produced from the wide area, resulting in a decrease in image resolution.

Accordingly, while the image resolution of the secondary electron image is due to the composition of the two events of electron beam probe size and electron diffusion in specimen, atomic resolution has not been achieved in conventional secondary electron images.

(ii-2) Three-Dimensional Information of Secondary Electron Image

As a technique for observing a three-dimensional surface structure, namely a topographic observation technique, an observation technique based on the use of secondary electrons has been conventional used. In the conventional secondary electron image, the secondary electrons are emitted from the depth on the order of 2 to 10 nm from the specimen surface layer, depending on the material. The emitted electrons characteristically provide a contrast dependent on the specimen surface morphology because of the effect of increased signal intensity from specimen edge portions according to a cosine angular distribution similar to Lambert's cosine law, for example. Thus, the secondary electron image strongly reflects the three-dimensional information of the specimen.

PRIOR ART DOCUMENTS

Patent Documents

Patent Document 1: JP Patent Publication (Kokai) No. 5-299048 A (1993)
Patent Document 2: JP Patent Publication (Kokai) No. 2006-49161 A Non-Patent Document Non-patent Document 1: Yimei Zhu, Hiromi Inada, Kuniyasu Nakamura, and Joseph Wall, "Imaging single atoms using secondary electrons with an aberration corrected electron microscope", Nature Materials, 8, 808-812 (2009)

SUMMARY OF THE INVENTION

Problem to be Solved by the Invention

As described above, (i) the forward scattered electron image and transmission electron image and (ii) the secondary electron image have different properties from the viewpoint of image resolution and three-dimensional information.

Conventionally, atomic resolution has not been obtained in the secondary electron image. However, it has been found by the present inventors that, as discussed in Non-patent Document 1, a secondary electron image of atomic resolution can be observed even with a scanning electron microscope by decreasing the irradiation electron beam size. This has enabled an application of the scanning (transmission) electron microscope based on the secondary electron image of atomic resolution.

Patent Document 1 provides an electron beam device that enables generation and measurement of a three-dimensional image of a specimen with surface roughness. While the electron beam device provides three-dimensional specimen information by varying electron beam focus conditions, it has not been able to provide a three-dimensional image identifying atoms.

In Patent Document 2, in order to obtain a three-dimensional structure of a specimen, the electron beam is inclined when the specimen is observed, and a stereoscopic image is obtained by combining a separate observation technique, such as atomic force microscopy (AFM) or scanning tunneling microscopy (STM). However, a three-dimensional image of atomic resolution cannot be obtained.

Objects of the present invention include enabling (a) three-dimensional observation of a 0.1 nm atomic size structure by a scanning (transmission) electron microscope; and (b) identification of three-dimensional structure of atoms and material of a specimen by the scanning (transmission) electron microscope.

Means for Solving the Problem

The present invention includes, as the major features, an electron lens system having a small spherical aberration coefficient for enabling three-dimensional observation of a 0.1 nm atomic size structure; an aperture capable of changing an illumination angle; an illumination electron lens system capable of changing the probe size of an electron beam probe and the illumination angle; a secondary electron detector; a transmission electron detector; a forward scattered electron beam detector; a focusing unit; an image processor for identifying image contrast; an image processor for computing image sharpness; a processor for three-dimensional reconstruction of an image; and a mixer for mixing a secondary electron signal and a specimen forward scattered electron signal.

Effects of the Invention

An advantage of a charged particle instrument according to the present invention is that because of the use of secondary electrons enabling identification of atoms, an atomic size three-dimensional observation can be performed.

Another advantage is that in a field of view such that the specimen as the object for observation exists in a superposed manner on the axis of observation in the depth direction, a structure inside the specimen can be easily visualized.

Another advantage is that, because of the use of the secondary electrons enabling identification of atoms and the specimen forward scattered electrons that form an element-dependent contrast, differences in elements of the surface atoms at an atomic size, or differences in material of an object of not more than 1 nm can be identified.

BRIEF DESCRIPTION OF DRAWINGS

FIG. 18 is a diagram illustrating a table recording pixel-by-pixel optimum focal depth and illumination angle, and condenser lens current.

MODE FOR CARRYING OUT THE INVENTION

First, the principle of the present invention will be described.

(a) With regard to enabling three-dimensional observation of a 0.1 nm atomic size structure in a scanning (transmission) electron microscope, the present invention achieves the object by obtaining an atomic resolution in a secondary electron image.

The principle of obtaining the atomic resolution in a secondary electron image will be described.

Conditions for observing an atomic resolution image in a secondary electron image include (1) the divergence of primary electron beam in the specimen is small, and the interaction volume with the specimen is small; (2) the spherical aberration of the objective lens is made extremely small, so that the electron beam probe size can be adjusted to subnanometer size; (3) the illumination angle of the electron beam is large, and the focal depth is shallow; and (4) the probe current is large and can produce a sufficiently large amount of secondary electrons for detection.

With regard to (1), as the energy (acceleration voltage) of the primary electrons is sufficiently increased, the interaction between the specimen and the electron beam becomes small. For example, in the case of electron beam with the acceleration voltage on the order of 20 kV, the electron beam is diffused to 200 to 300 nm at the specimen depth of 100 nm, while in the case of the acceleration voltage of 200 kV, the diffusion is less than 10 nm. With regard to (2) to (4), the conditions are achieved by decreasing the size of the electron beam probe by using a spherical aberration corrector. Thus, by increasing the acceleration voltage of the primary electron beam by using an aberration corrector, a secondary electron image having an atomic resolution can be obtained.

(b) With regard to enabling the identification of a three-dimensional structure of atoms and material of a specimen in a scanning (transmission) electron microscope, the object is achieved by the present invention by combining information of a secondary electron image having an atomic resolution and a forward scattered electron image or a transmission electron image.

Figure 12:
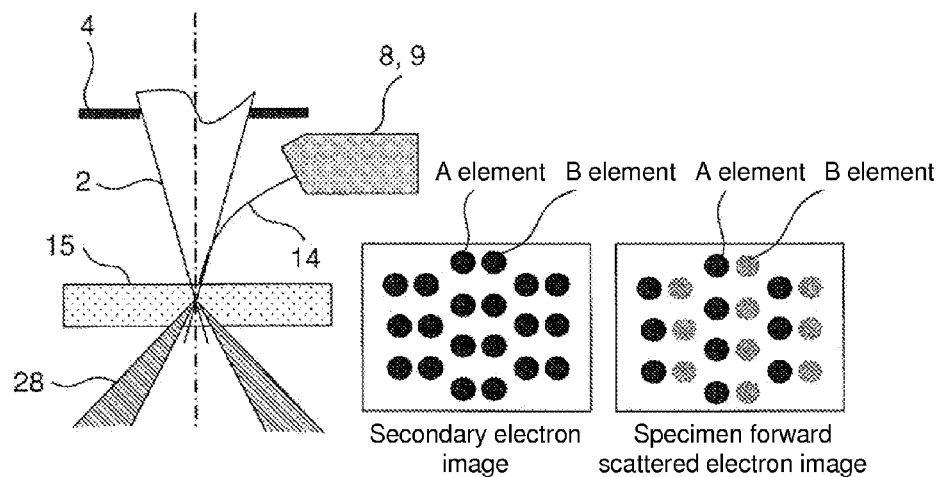
FIG. 12 shows a schematic of a configuration of an incident electron beam, specimen forward scattered electrons produced, secondary electrons, and their detectors, and diagrams illustrating a difference in contrast between a secondary electron image and a specimen forward scattered electron image of a specimen image including two kinds of elements A and B observed at a magnification ratio of atomic resolution.

While the specimen scanning magnified image by secondary electrons provides a contrast reflecting the surface structure, the atomic number dependence of the contrast is small. As described above, although it has become possible to observe a secondary electron image of atomic resolution with the scanning electron microscope, since the secondary electron atomic image does not have an atomic number-dependent contrast, various elements existing in the field of view could not be identified. FIG. 12 schematically shows the difference in contrast due to the difference in elements in a case where a secondary electron image and a dark field of view STEM image were simultaneously photographed. Thus, by combining information of the secondary electron image having an atomic resolution and the forward scattered electron image or the transmission electron image, it has become possible to identify the three-dimensional structure of atoms in the specimen and its material.

In the following, a specific embodiment of the present invention will be described.

EXAMPLE 1

Figure 1:
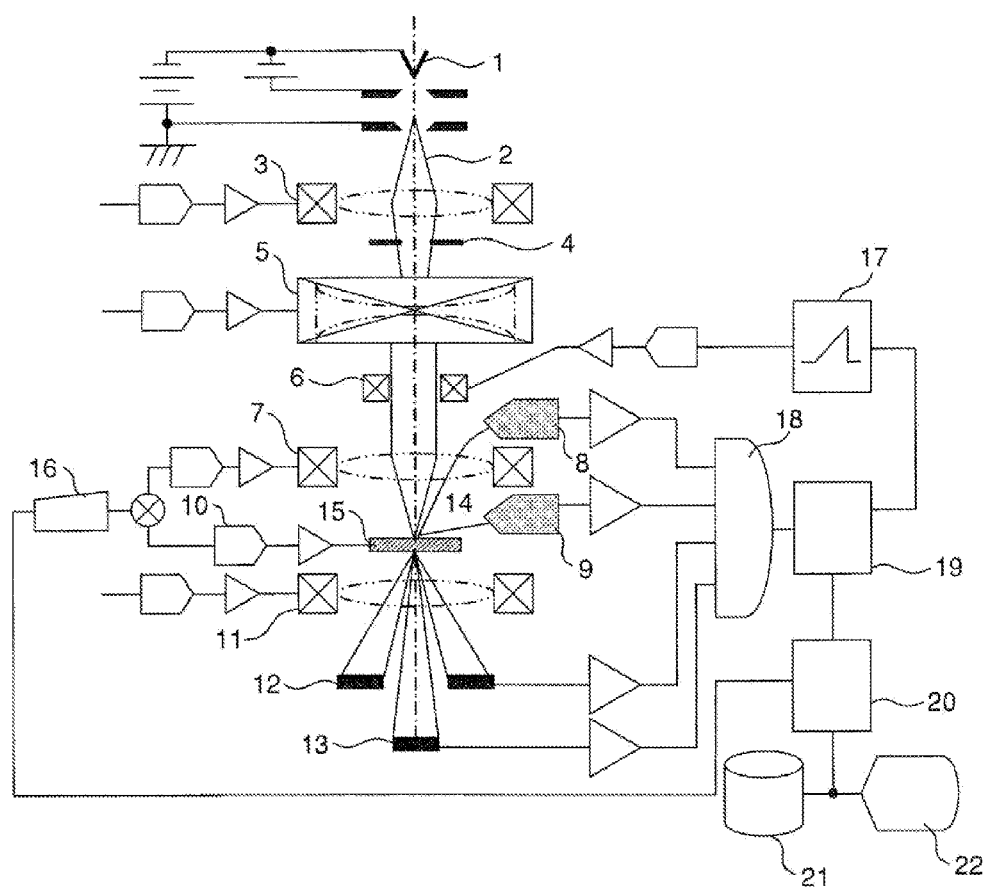
FIG. 1 is a diagram illustrating a method of implementing a charged particle instrument according to the present invention.

FIG. 1 is a schematic diagram illustrating an example of a charged particle according to the present invention.

A primary electron beam 2 generated by an electron gun 1 is condensed by a condenser lens 3 and passed through an aperture 4. While, in FIG. 1, the condenser lens is shown to have one stage for simplicity's sake, the condenser lens may have two stages for changing the illumination angle, or three or more stages for changing the illumination angle while the demagnification of an electron source produced by the electron gun is fixed. The aperture 4 may be set to an arbitrary aperture diameter for obtaining a desired illumination angle on the specimen surface. The illumination angle of the electron beam with which the specimen is irradiated is determined by the aperture diameter. While the aperture is positioned in a subsequent stage to the condenser lens, the installed position is not particularly limited for the purpose of changing the illumination angle.

In order to decrease the beam size of the primary electron beam 2 at the specimen position to 0.1 nm or less, an aberration corrector 5 for correcting spherical aberration of the objective lens 7 is mounted. The aberration corrector 5 may have various configurations depending on the combination of multipole lenses used. According to the present invention, the structure may include a hexapole type or a complex quadrupole-octupole type as long as there is one electron lens on the electron beam incident side of the spherical aberration corrector. The electron beam probe size indicated by expression 1 is equivalent to making the first term, which is the spherical aberration term, to zero. Generally, it is difficult to form an electron beam with a shallow focal depth when an electron beam probe of 0.1 nm diameter is formed because of the influence of spherical aberration of the electron lens. For this reason, the aberration corrector is used. Further, when the spherical aberration of the electron lens is corrected by using the aberration corrector, it becomes possible to produce a primary electron beam that is not influenced by spherical aberration in an off-axis area from the optical axis of the electron beam. Thus, an electron beam with a large illumination angle can be provided, and the focal depth can be made shallower.

The specimen is scanned with the primary electron beam 2 by the electron beam scanning unit 6. The scan direction is in accordance with a current waveform generated by a scanning signal generator 17. The structure of the electron beam scanning unit 6 may be based on a magnetic field or an electric field.

The primary electron beam 2 irradiating the specimen 15 after being narrowed to a minute size by the objective lens 7 produces secondary electrons 14, which are detected by an upper secondary electron detector 8 or a lower secondary electron detector 9. While the example shown in FIG. 1 includes the two, an upper and a lower, secondary electron detectors, there may be one detector. Structurally, the detector may include a detector including a phosphor and a photomultiplier, or a semiconductor detector. While not shown in FIG. 1, an energy filter for electron beam energy discrimination, or a secondary electron/reflected electron discriminator using an electromagnetic field, may or may not be disposed between the secondary electron detector and the specimen.

Transmission electrons and forward scattered electrons that have passed through the specimen 15 are detected by the forward scattered electron detector 12 and the transmission electron detector 13 disposed below the specimen 15. The various signal electron beams detected by the detectors are inputted to a signal mixer 18 via respective amplifier circuits, and the secondary electrons and a desired transmission signal are selected. The signal that that has passed through the signal mixer 18 is synchronized with a scanning signal in a signal synchronizer 19 to form a scanning image.

The focus of the electron beam with which the specimen is irradiated is adjusted by a focusing unit 16 that controls the objective lens 7 or a specimen stage motion mechanism 10 driving the specimen stage. Each time the focus is changed by a focusing step of not more than the focal depth of the secondary electron, a specimen scanning magnified image is recorded in the recording unit. The magnified images at each focusing step are stacked, and reconstructed into a three-dimensional image by an image processor 20. Secondary electron signals from a specimen surface structure and a structure existing in the depth direction are detected by varying the electron beam illumination angle by the aperture or the power of the condenser lens, and recorded in the recording unit as a secondary electron scanning image.

The reconstructed image is recorded in the image recording unit 21, and also displayed by the image display unit 22. The contrast of the specimen forward scattered electrons is evaluated by the image processor 20, a contrast threshold value for each element is determined, and the contrast is composed with the secondary electron scanning image. The composition image is recorded in the image recording unit 21, or displayed by the image display unit 22.

Figure 10:
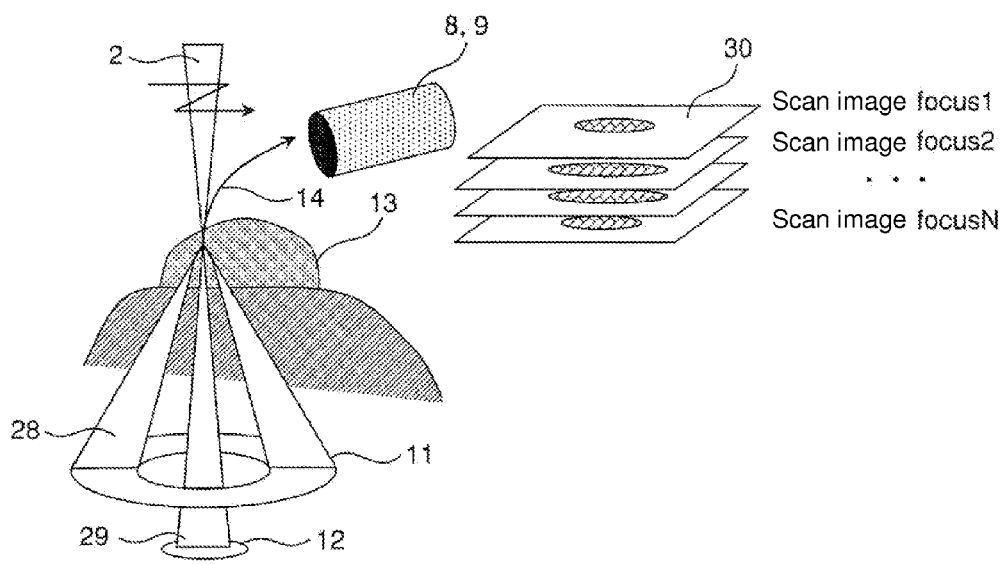
FIG. 10 is a diagram illustrating an incident electron beam, various signal electrons produced, and a series of scan images obtained by varying focus.

FIG. 10 is a diagram illustrating the incident electron beam, various signal electrons generated, and a series of scan images obtained by varying focus.

The primary electron beam 2 narrowed to a size on the order of 0.1 nm irradiates the specimen 15 and scans the specimen 15. The electron beam interacts with the specimen and produces the secondary electrons 14, which are detected by the upper secondary electron detector 8 or the lower secondary electron detector 9. The electrons that have passed through the specimen are divided into forward scattered electrons 28 and transmission electrons 29, depending on their angle of detection. The transmission electrons 29, which are due to inelastic scattering along the electron beam optical axis, are detected by the transmission electron detector 13. The forward scattered electrons 28, which are due to elastic scattering by the specimen, are detected by the forward scattered electron detector 12. The detection signals are synchronized with the scan waveform and temporarily recorded as two-dimensional scan images photographed at arbitrary focusing steps, with sequential designations focus1, focus2, . . . , and so on, for example. The secondary electrons produced from the specimen, and the forward scattered electrons or the transmission electrons are simultaneously detected and recorded.

Figure 2:
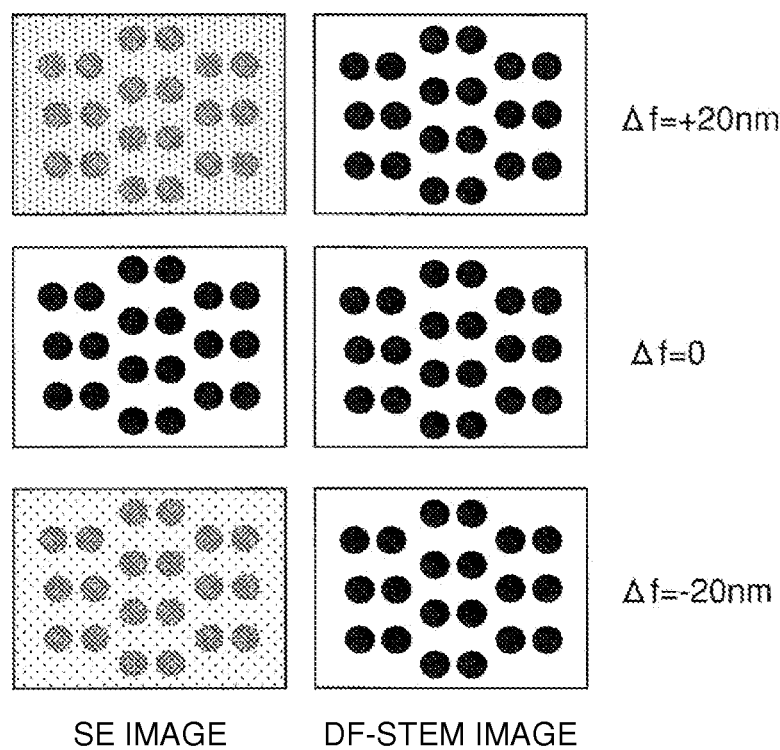
FIG. 2 is a diagram illustrating changes in image contrast as a result of focus change in a secondary electron image and a specimen forward scattered electron image.
Figure 11:
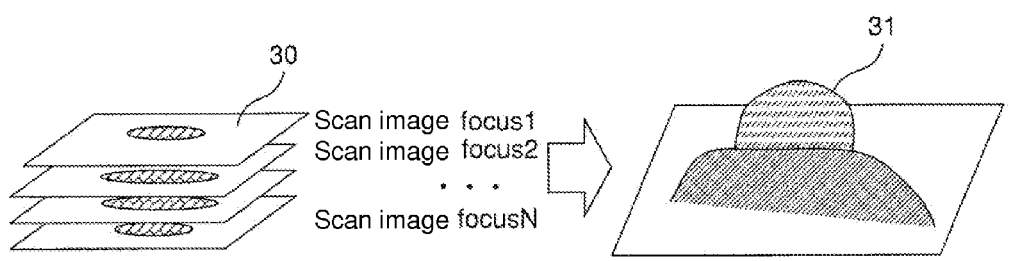
FIG. 11 is a diagram illustrating reconstruction of a three-dimensional image from the series of scan images obtained by varying focus.

FIG. 2 is a diagram illustrating changes in image contrast as a result of focus change in the secondary electron image and the forward scattered electron image, showing changes in focal depth of the secondary electrons and the forward scattered electrons. Based on the result of an experiment of focus dependence of an atomic image by secondary electrons, the focal depth of secondary electrons is shallow compared with a forward scattered electron image. This is due to the fact that the contrast of the forward scattered electrons is attributable to channeling contrast whose intensity is increased by the atomic columns. Based on the characteristics that the focal depth of the secondary electron image having an atomic resolution is shallow, and by superposition of the defocus series of scan images shown in FIG. 10, a three-dimensional structure is reconstructed as shown in FIG. 11, which illustrates an example of the present invention. The three-dimensional image is reconstructed with the atomic resolution secondary electron image alone. As a reconstruction method, an electron beam computed tomography (CT) process may be used. The secondary electron image photographed under the atomic image observation conditions according to the present invention, with a shallow focal depth and while varying the focus, can be obtained as slice images reflecting the structure of each layer. Thus, a plurality of such slice images are recorded and reconstructed into the three-dimensional image through computation.

When the reconstruction is performed with the secondary electron image alone, an atomic image from the vicinity of the specimen surface can be three-dimensionally observed simultaneously with the contrast reflecting the specimen surface form, which is a characteristic of secondary electrons. It is also possible to observe a stereoscopic structure of an object on the order of a single atom layer. When the three-dimensional structure is reconstructed based on a superposition of the secondary electron image and the simultaneously photographed transmission electron or forward scattered electron signal, it is possible to reconstruct not only the surface structure by the secondary electrons, but also a three-dimensional structure reflecting the state of crystalline structure extending in the depth direction of the specimen.

EXAMPLE 2

Next, an example of obtaining a two-dimensional electron image by varying the focal depth will be described.

Figure 3:
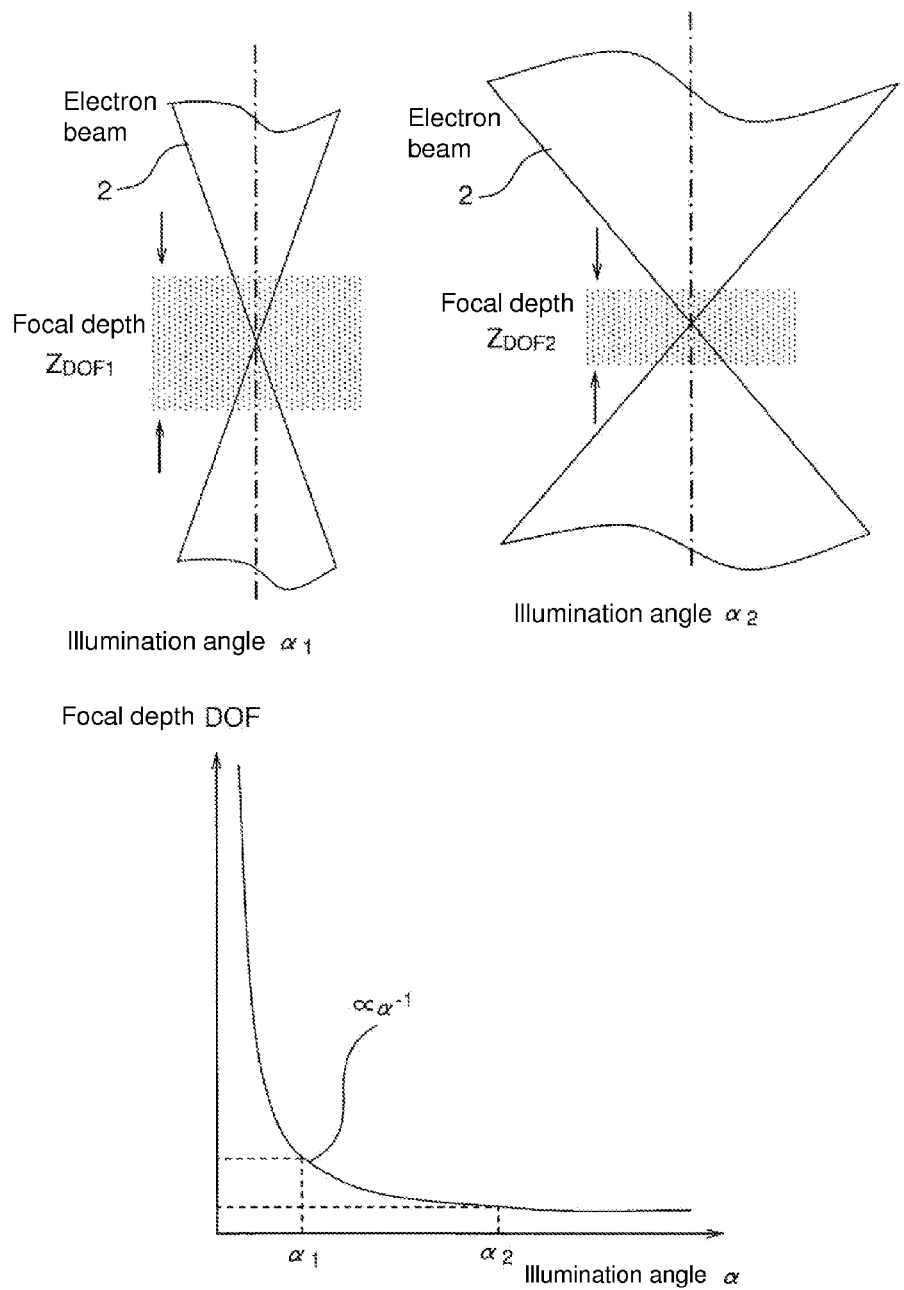
FIG. 3 shows diagrams illustrating the relationship between electron beam illumination angle and focal depth.

First, the relationship between the illumination angle and focal depth of the primary electron beam probe will be described with reference to FIG. 3. The focal depth $Z_{DOF}$ of the electron beam probe size d at the illumination angle $\alpha$ is expressed by expression 2.

[Expression 2]

$$Z_{DOF} = \frac{d}{\alpha} \quad \text{Expression 2}$$

Thus, when the electron beam probe size d is fixed, the focal depth becomes shallower as the illumination angle of the electron beam is increased. Accordingly, in order to double the focal depth, the electron beam illumination angle may be halved.

Figure 4:
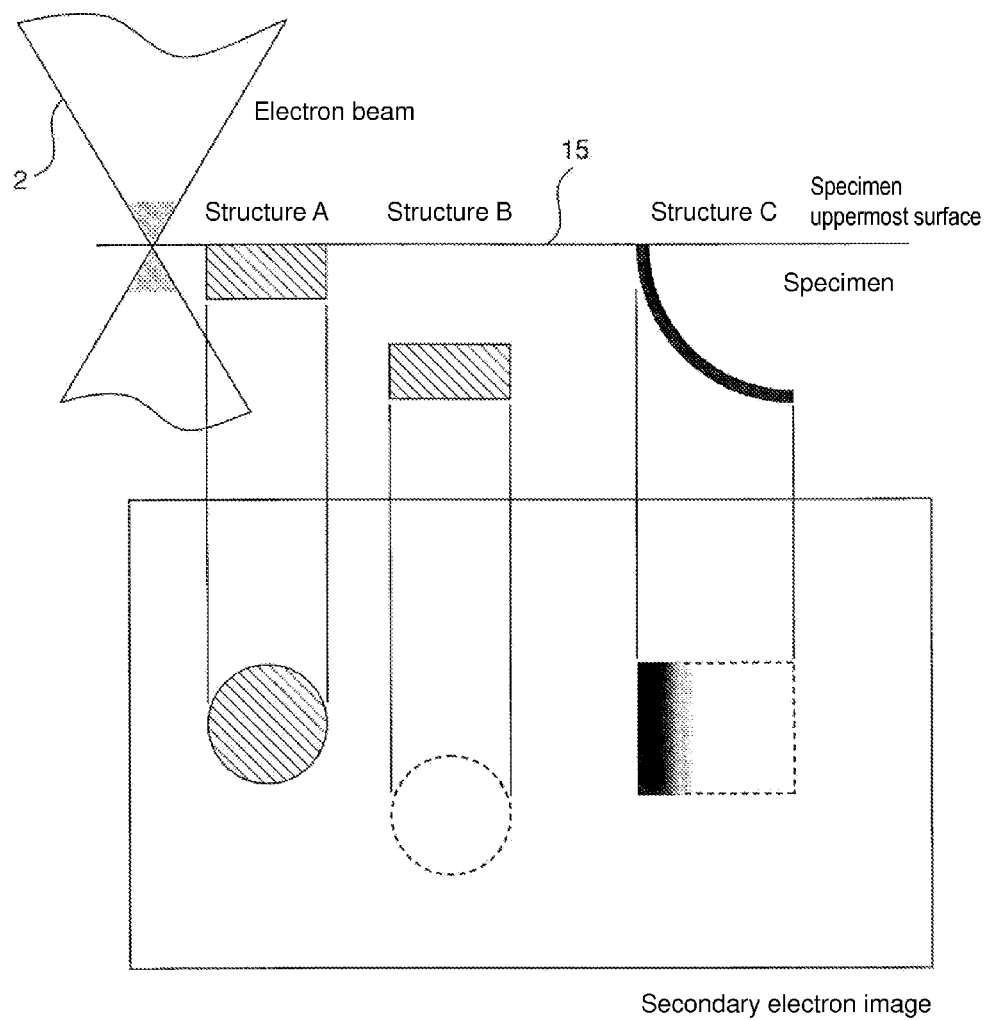
FIG. 4 is a diagram illustrating the relationship between an incident electron beam on specimen and a secondary electron image from the specimen having structures in the depth direction of the incident electron beam.

FIG. 4 is a diagram illustrating the relationship between the incident electron beam on the specimen and a secondary electron image of the specimen, which has structures in the depth direction of the incident electron beam. For example, a structure A has an elemental composition in the specimen surface layer portion different from the others; a structure B has an elemental composition inside the specimen different from the others; and a structure C arcs inward from the specimen surface layer. The structure A has a depth of 2 nm in the depth direction. The structure B is positioned at the depth of approximately 20 nm from the surface, and has a depth of 2 nm in the depth direction.

When a scan is performed with an increased illumination angle of the electron beam and a decreased focal depth while being focused at the specimen surface, a signal of secondary electrons from the structure A at the surface layer portion can be acquired. However, hardly any signal from the structure B inside the specimen can be captured. Further, in the case of the structure C, because the image is formed only by a signal from the vicinity of the surface layer, the secondary electron image has a gradation, as shown.

On the other hand, in the case of an image formed by the transmission electrons or the specimen forward scattered electrons, all of the signals from the structures existing in the specimen depth direction are projected, so that the positions of the structures A, B, and C in the specimen in FIG. 4 cannot be clearly specified.

Thus, in the present example, the acceleration voltage of the primary electron beam is increased so that there is hardly any interaction between the primary electron beam and the specimen (a state such that there is little influence of diffusion of the primary electrons in the specimen), the illumination angle is decreased, and the focal depth is increased, whereby it becomes possible to observe the specimen with the structure A at the specimen surface layer portion, the structure B inside the specimen, and the structure C extending inside from the specimen surface layer portion all in focus.

For example, when the electron beam acceleration voltage is set at a high voltage on the order of 200 kV, the electron beam enters the inside of the specimen with hardly any interaction between the primary electron beam and the specimen, so that the influence of diffusion of primary electrons in the specimen is suppressed. Further, by decreasing the illumination angle and increasing the focal depth, it becomes possible to form an image of a signal from inside the specimen, such as from the structure B.

The secondary electrons may be roughly classified into four types, called SE1, SE2, SE3, and SE4, depending on their originating source. SE1 refers to secondary electrons produced by direct interaction between the primary electron beam and the specimen. SE2 refers to secondary electrons secondarily produced by specimen backscattered electrons (reflected electrons) produced by the primary electron beam. SE3 refers to secondary electrons produced by the specimen backscattered electrons (reflected electrons) acting on a member inside the electron microscope. SE4 refers to secondary electrons produced by the primary electron beam acting on a member inside the electron microscope. Because the backscattered electrons are caused by elastic scattering, the backscattered electrons have substantially the same energy as the energy of the incident primary electron beam. The signal of the internal structures of the specimen that is observed by increasing the focal depth includes the backscattered electrons themselves that have passed through the specimen, SE2, SE3, and SE1. While the secondary electrons of the structure in the specimen surface layer portion are mainly due to SE1, the secondary electrons produced by the internal structures of the specimen may possibly be SE1, SE2, or SE3, or a composition thereof, and cannot be clearly distinguished.

In the secondary electron image obtained by the present example, the structures A to C are all in focus, and the mutual positional relationship in the depth direction is also recognizable. However, differences in constituent elements of the structures A to C cannot be obtained.

EXAMPLE 3

Figure 5:
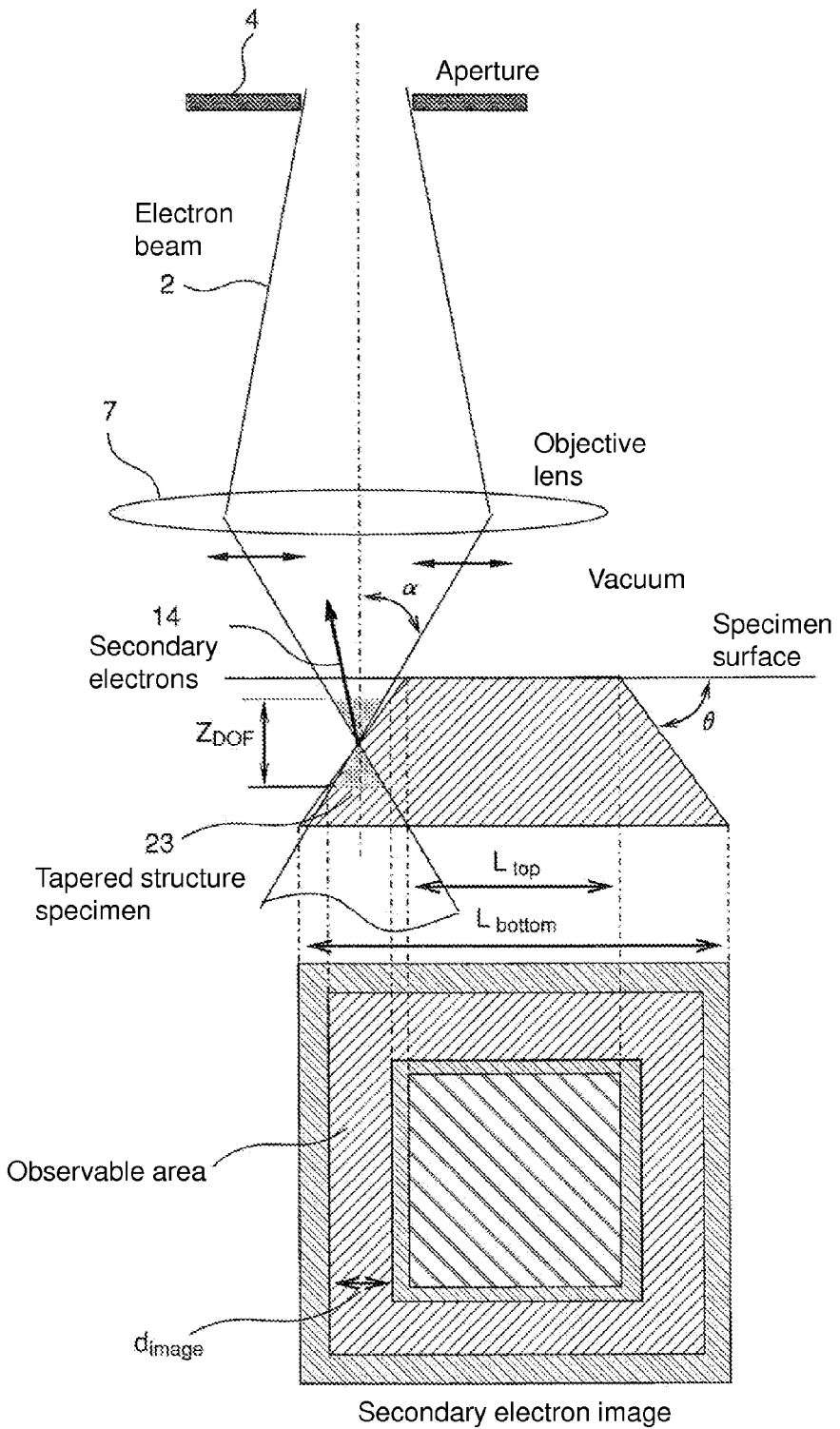
FIG. 5 is a diagram illustrating the relationship between a specimen having a taper structure and the incident electron beam.

FIG. 5 is a diagram illustrating the relationship between a specimen having a tapered structure and the electron beam incident thereon. By using the specimen with the tapered structure, the magnitude of focal depth and the amount of defocus can be measured. The specimen is fabricated and prepared by designing the size of the structure such that, for example, the length of the specimen uppermost surface is Ltop, the length of the specimen lowermost surface is Lbottom, and the taper angle is θ. The specimen with the tapered structure may be fabricated through epitaxial growth of different materials on a single crystal wafer by a manufacturing technique such as sputtering (physical vapor deposition), chemical vapor deposition (CVD), or molecular beam epitaxy (MBE), followed by selective etching of specific areas.

The focal depth measurement is performed as follows. Under the condition that the focal depth at the illumination angle α is $Z_{DOF}$, a secondary electron image is generated while scanning the electron beam. A signal from a taper portion provides a secondary electron image focused with the width of $d_{image}$, so that actual measurement of the focal depth can be made based on the size of the taper structure specimen according to design. In FIG. 5, the focal depth $Z_{DOF}$ is determined by expression 3.

[Expression 3]

$$Z_{DOF} = \frac{d_{image}}{\tan\theta} \quad \text{Expression 3}$$

The amount of defocus is measured as follows. An objective lens current value is set such that the electron beam is focused at the uppermost surface, and this point of focus is taken as the correct focal point position. While the electron beam is scanned, a secondary electron image is generated. At this time, the size of the structure portion is substantially equal to Ltop. After the two-dimensional scan of the specimen surface is completed, the objective lens coil excitation current is changed, a secondary electron image is generated, the size of the structure portion is measured, and then a defocus value can be determined by comparing the objective lens current value with the size from the structure portion. While the objective lens coil excitation current is changed as a defocus method in the present example, a method of changing the height of the specimen stage may be adopted. The defocus value can be more accurately measured by performing the measurement when the focal depth is shallow.

When the specimen has the same composition as the object for observation, the evaluation can be made under conditions approximating actual conditions, whereby the accuracy of quantitative evaluation of the focal depth and the amount of defocus can be further increased.

The specimen may be mounted on the scanning transmission electron microscope according to the present invention, and the relationship between the electron beam defocus and the image signal and/or the relationship between the focal depth of the electron beam and the observable image signal can be evaluated by using the present specimen. Further, there can be provided a scanning transmission electron microscope such that, using the specimen, the relationship between the amount of defocus and image contrast can be determined in advance by quantitatively evaluating the defocus of the electron beam by varying the intensity of the objective lens or the height of the specimen stage, and the image contrast of the simultaneously observed secondary electron image. Further, there can be provided a scanning transmission electron microscope such that, using the specimen, the relationship between the focal depth and image contrast can be determined in advance by varying the focal depth of the electron beam by varying the electron beam illumination angle by changing the size of the aperture or the power of the converging lens, and quantitatively evaluating the image contrast of the simultaneously observed secondary electron image.

The image contrast may be quantitatively evaluated by various methods. For example, in a method, the evaluation is based on the sum of signal intensity of each pixel of a two-dimensional digitalized image. In another method, image sharpness may be determined. In the following, the method involving determining image sharpness will be described.

The image sharpness giving image sharpness of an M×N two-dimensionally digitalized image is given by the following computation.

[Expression 4]

$$\nabla f(x, y) = \frac{\partial f(x, y)}{\partial x} + \frac{\partial f(x, y)}{\partial y} \quad \text{Expression 4}$$
$$= f_x(x, y) + f_y(x, y)$$

A first-order differentiation of the two-dimensional image can be indicated by the difference from an image with a one-pixel displacement of the image pixels, and can therefore be given by the following expression.

[Expression 5]

$$f_x(i,j) = f(i+1,j) - f(i,j)$$
$$f_y(i,j) = f(i,j+1) - f(i,j) \quad \text{Expression 5}$$

Similarly, a second-order differentiation of the image can be given by the following expression.

[Expression 6]

$$\nabla^2 f(x, y) = \frac{\partial^2 f(x, y)}{\partial x^2} + \frac{\partial^2 f(x, y)}{\partial y^2} \quad \text{Expression 6}$$
$$= f_{xx}(x, y) + f_{yy}(x, y)$$

The image sharpness G is indicated by the mean square of the components x and y indicated by the following expression.

[Expression 7]

$$Gx = (\text{original image}) - (x \text{ component of first-order differentiation}) \quad \text{Expression 7}$$

[Expression 8]

$$Gy = (\text{original image}) - (y \text{ component of first-order differentiation}) \quad \text{Expression 8}$$

[Expression 9]

$$G = \sqrt{G_x^2 + G_y^2} \quad \text{Expression 9}$$

The mean of the image sharpness is:

[Expression 10]

$$G_{Avg} = \frac{\sum_x \sum_y G(x, y)}{M \times N} \quad \text{Expression 10}$$

Dispersion V and the standard deviation 6 are indicated by the following expressions.

[Expression 11]

$$V = \frac{\sum_x \sum_y [G(x, y) - G_{Avg}]^2}{M \times N} \quad \text{Expression 11}$$

[Expression 12]

$$\sigma = \sqrt{V} \quad \text{Expression 12}$$
$$= \sqrt{\frac{\sum_x \sum_y [G(x, y) - G_{Avg}]^2}{M \times N}}$$

The standard deviation of the image sharpness of the two-dimensional image is used as an index of the sharpness of the image. By using the image sharpness, an appropriate setting value as an evaluation index for the electron beam defocus or focal depth is finalized.

EXAMPLE 4

The method of changing the illumination angle of the electron beam without changing the electron beam probe size includes two techniques, as will be illustrated with reference to FIGS. 6 and 7.

Figure 6:
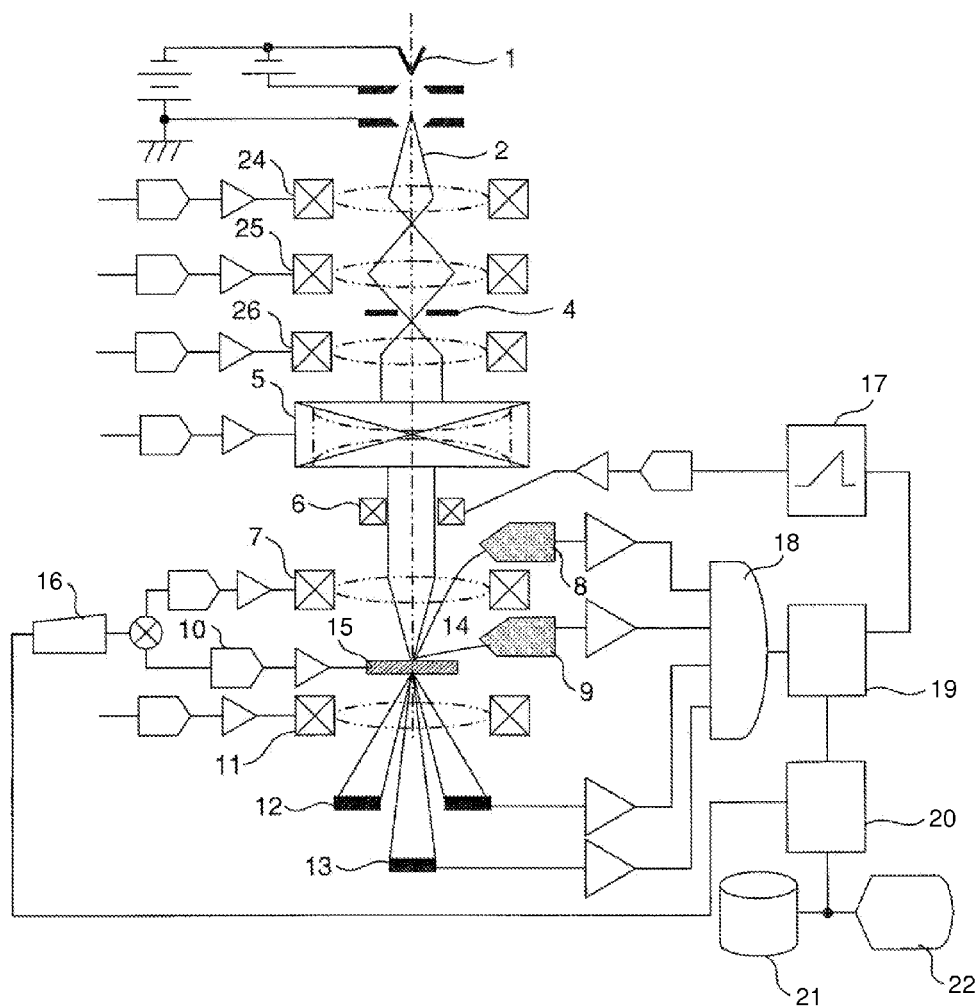
FIG. 6 is a diagram illustrating an example of a charged particle instrument according to the present invention having an optical system such that the electron beam illumination angle can be varied without changing the probe size of the electron beam irradiating the specimen.

FIG. 6 is a diagram illustrating an example of a charged particle instrument according to the present invention having an optical system that can change the electron beam illumination angle without changing the probe size of the electron beam with which the specimen is irradiated. The present configuration is characterized in that three stages of condenser lenses are provided in a stage preceding the aberration corrector. This configuration enables varying the illumination angle while maintaining a constant virtual source size of the electron gun. An electron lens mounted on the aberration corrector may be used as a third condenser lens 26. The condenser electron lens excitation intensity is given by varying the current value applied to an electromagnetic coil. The other elements shown in FIG. 6 are similar to those of the system diagram shown in FIG. 1; thus, a detailed description of the similar elements will be omitted.

Figure 7:
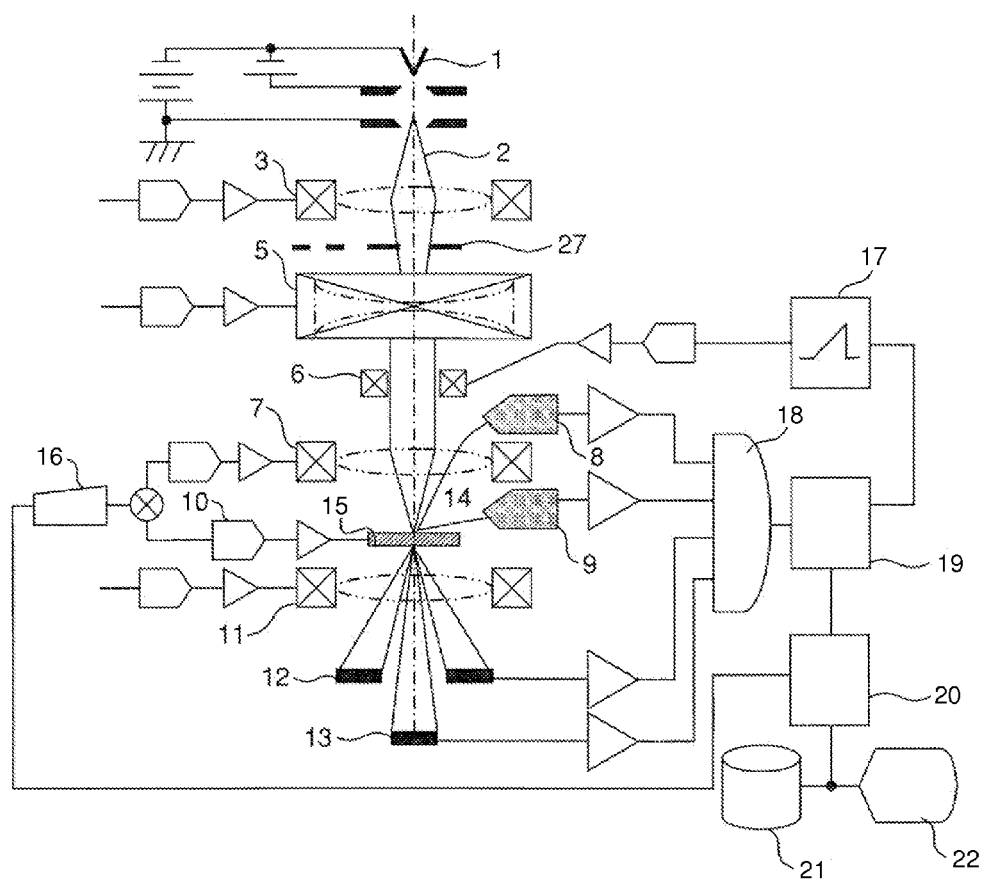
FIG. 7 is a diagram illustrating an example of the charged particle instrument according to the present invention having an optical system such that the illumination angle of the electron beam irradiating the specimen can be arbitrarily varied by changing the opening size of an aperture.
Figure 8:
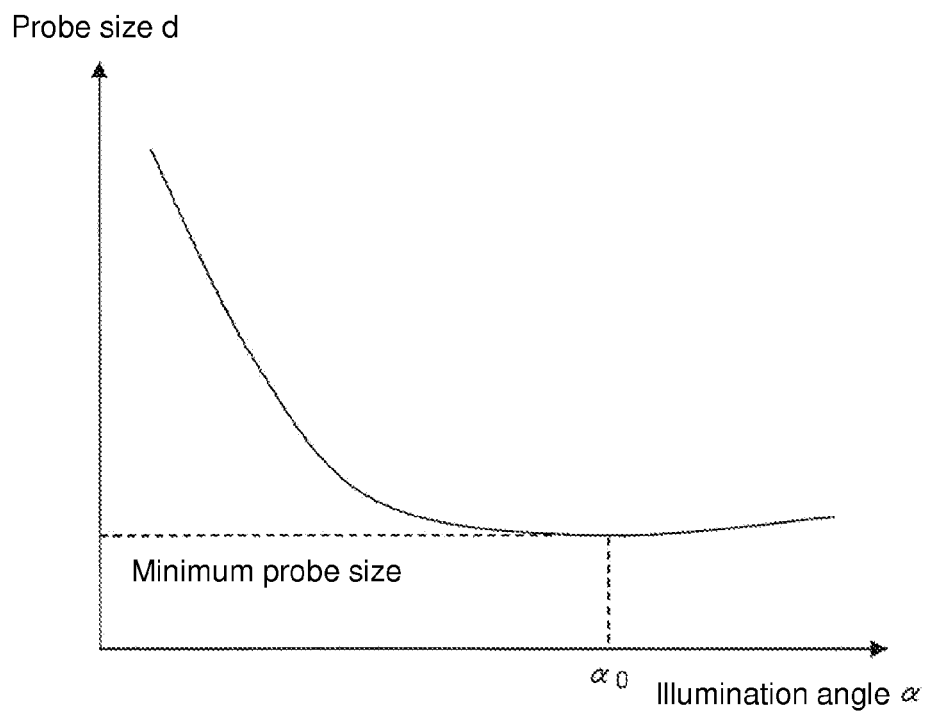
FIG. 8 is a diagram illustrating the relationship between electron beam illumination angle and electron beam probe size.

FIG. 7 is a diagram illustrating an example of the charged particle instrument according to the present invention having an optical system that can arbitrarily vary the illumination angle of the electron beam with which the specimen is irradiated by changing the opening size of the aperture. The present configuration is characterized in that an aperture 27 inserted at a condenser lens has a plurality of hole sizes. This configuration enables varying the illumination angle while maintaining the electron beam probe size under the condition of no influence of diffraction aberration. A greater number of hole sizes in the aperture enables setting the illumination angle in more various ways. The other elements shown in FIG. 7 are similar to those of the system diagram shown in FIG. 1; thus, a detailed description of the similar elements will be omitted.

EXAMPLE 5

Figure 9:
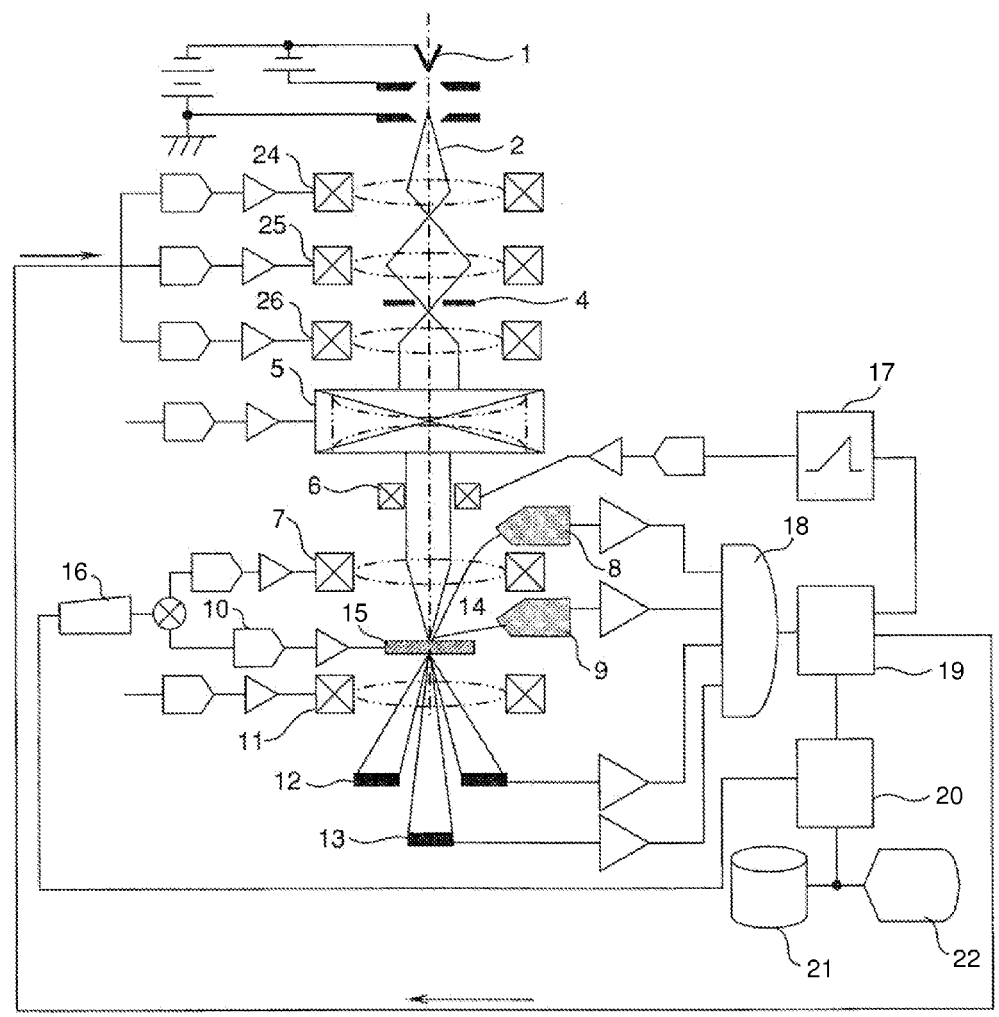
FIG. 9 is a diagram illustrating a method of implementing the present invention including extracting information from a specimen depth direction while changing the electron beam illumination angle such that an optimum contrast can be automatically obtained, and forming a two-dimensional specimen magnified image.

An example according to the present invention in which, using the above techniques, information from the specimen depth direction is extracted in such a way that contrast is automatically optimized, and a two-dimensional specimen magnified image is formed will be described with reference to FIG. 9.

The present configuration is characterized in that first to third condenser lenses 24, 25, and 26 are controlled such that the illumination angle can be adjusted to an optimum value on a pixel unit basis by associating the position information of the two-dimensional scan image obtained by the image processor 20 with the setting of the illumination angle of the electron beam probe by a signal synchronizer 19.

According to the present example, the illumination angle for each pixel that is set in advance is recorded with respect to the pixel-unit position information of the two-dimensional scan image, so that an illumination angle 1 can be set for one pixel by controlling the first to third condenser lenses, while an illumination angle 2 can be set for another pixel by controlling the first to third condenser lenses, for example. In this configuration, observation can be made while the illumination angle is dynamically changed as the specimen is scanned with the electron beam probe. Thus, while an atomic image of the specimen surface is being observed at high resolution, structures inside the specimen can also be observed while the electron beam probe size is maintained. At this time, the primary electron beam is scanned with the focus position fixed at the specimen surface position. This is because the way the image is viewed would be different if the primary electron focus position is changed to the inside of the specimen.

A detailed description of the other elements similar to those of the system diagram shown in FIG. 1 will be omitted.

Figure 15:
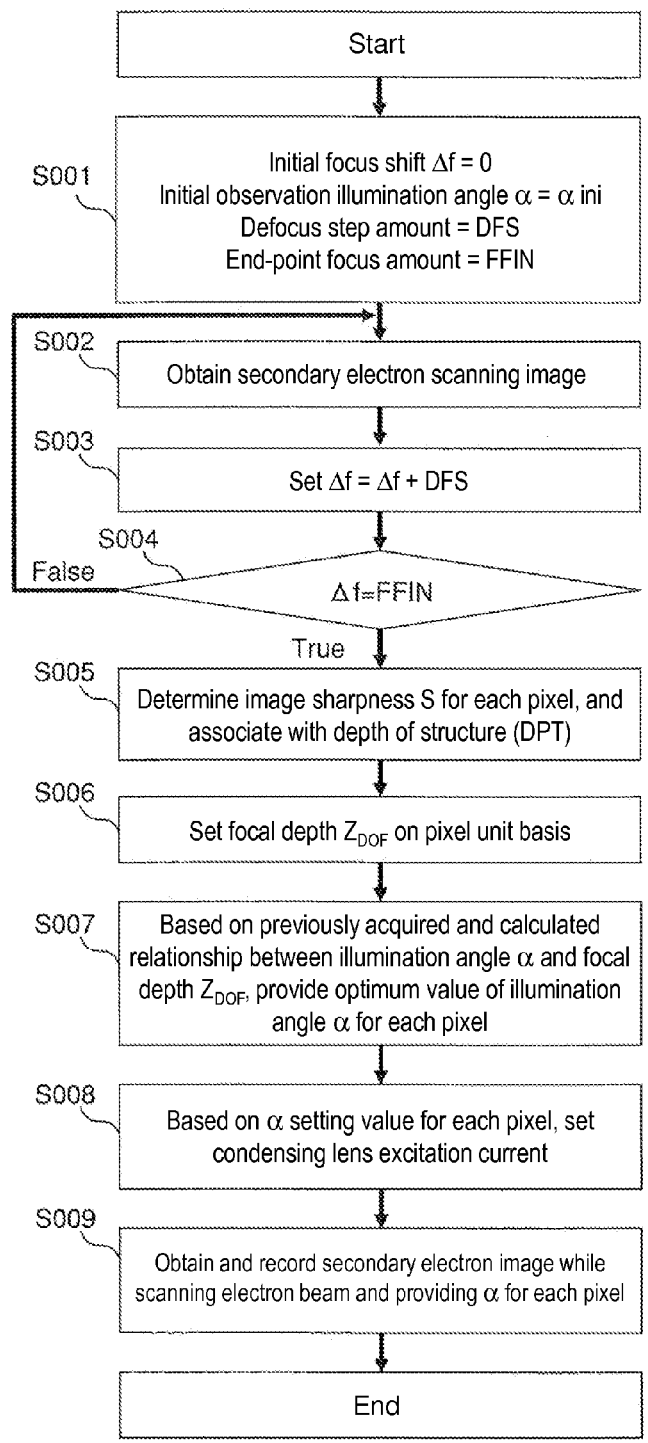
FIG. 15 is a flowchart of an example of the present invention in which information from the specimen depth direction is extracted while changing the electron beam illumination angle such that an optimum contrast can be obtained automatically, and a two-dimensional specimen magnified image is formed.

A flow of the present example is shown in FIG. 15.

In step S001, the initial conditions of the charged particle instrument are set. In the present example, the initial value of the amount of focusing shift $\Delta f=0$, the illumination angle $\alpha$ is the initial value $\alpha_{ini}$, the amount of defocusing step of the electron beam is DFS, and the final point of defocus is FFIN.

In step S002, based on the conditions set in S001, a two-dimensional secondary electron image generated by scanning the specimen as the object for observation with the electron beam is digitally recorded.

After the photographing, an amount of defocus corresponding to the amount of defocusing step DFS is added in step S003.

Figures 16, 17:
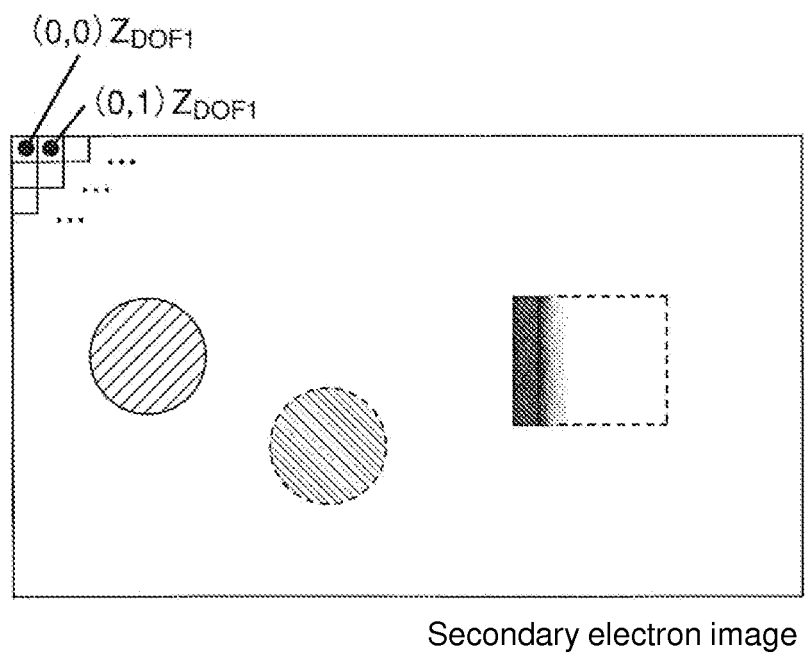
FIG. 16 is a diagram illustrating an image sharpness evaluation value table recording pixel position, defocus, and results of evaluation of image sharpness.
FIG. 17 is a conceptual diagram illustrating the pixel-by-pixel setting of a focal depth $Z_{DOF}$ in a two-dimensional digitalized secondary electron image.

Step S004 is a step of determining whether $\Delta f$ has reached the final point amount FFIN. When $\Delta f \neq FFIN$, steps S002 to S003 are repeatedly performed. When $\Delta f = FFIN$ in step S004, the process goes onto step S005. In step S005, the second-order differential value according to expression 6 is computed as a pixel-unit image sharpness for each pixel of the two-dimensional secondary electron digital image, and the depth DPT of the structure is determined. In order to associate the amount of defocus with the image sharpness S on a pixel-by-pixel basis, an image sharpness evaluation value table in which pixel position, defocus, and image sharpness evaluation result are recorded is prepared, as shown in FIG. 16.

In step S006, the structure depth DPT and the focal depth $Z_{DOF}$ are associated with each other, and the pixel-by-pixel focal depth $Z_{DOF}$ is set.

In step S007, based on the relationship between the previously acquired and calculated illumination angle α and the focal depth $Z_{DOF}$, an optimum value of the illumination angle α at each pixel is given.

In step S008, based on the pixel-by-pixel a setting values, the condenser lens excitation current is set. The setting in steps S006 to S008 will be described with reference to FIGS. 17 and 18. FIG. 17 shows a two-dimensional digitalized secondary electron image. The $Z_{DOF}$ evaluated in step S006 is associated on a pixel-by-pixel basis. FIG. 18 shows a table in which the pixel-by-pixel optimum focal depth and illumination angle, and condenser lens current are recorded. The numerical values computed in steps S007 and S008 are recorded in the table of FIG. 18.

In step S009, the electron beam is scanned, and a secondary electron image is photographed and recorded while giving a condenser lens excitation current value suitable for the illumination angle α set on a pixel-by-pixel basis as shown in FIG. 18.

By performing observation in accordance with the configuration and flow according to the present invention, in a field of view such that the specimen as the object for observation exists in a superposed manner on the axis of observation in the depth direction, the structures in the specimen can be easily visualized. Thus, a secondary electron image of atomic resolution not only from the specimen uppermost surface but also from structures existing inside the specimen can be simultaneously recorded as a single image.

EXAMPLE 6

Figure 13:
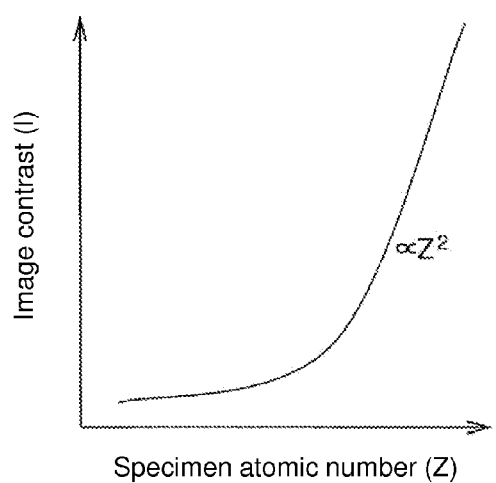
FIG. 13 is a graph indicating that the image contrast of specimen forward scattered electrons is a function of the atomic number of specimen.

FIG. 12 shows a schematic diagram illustrating an incident electron beam, specimen forward scattered electrons and secondary electrons produced, and their detectors, and diagrams illustrating the difference in contrast between a secondary electron image and a specimen forward scattered electron image of a specimen image including two kinds of elements A and B observed at a magnification ratio of atomic resolution. The incident primary electron beam 2 interacts with the specimen 15 and produces the secondary electrons 14. Elastic scattering electrons due to Rutherford scattering by the specimen are detected by the specimen forward scattered electron detector as specimen forward scattered electrons 28. When the angle of incidence on the forward electron detector, i.e., the angle of acquisition of the scattering angle is large, the contrast is the so-called Z-contrast, which is dependent on the specimen atomic number. An image acquired under such condition is referred to as a Z-contrast image. FIG. 13 shows the relationship between the specimen atomic number of the Z-contrast image and the image contrast. Generally, image contrast is proportional to approximately the square of the specimen atomic number Z. Thus, when different kinds of elements are present, the elements can be identified. As shown in FIG. 12, when the material of the specimen including elements A and B with different element numbers is magnified to a magnification such that the atoms can be identified by using the scanning electron microscope, the elements A and B cannot be identified because there is hardly any change in contrast of the secondary electron image due to the element number. It is now assumed that the element A is a heavy element and the element B is a light element. While in FIG. 12 the elements are indicated by black dots for illustration purposes, in the actual specimen magnified image, the black and white are reversed; namely, the heavier elements are displayed more lightly. Meanwhile, the illumination angle of the irradiation electron beam can be adjusted by adjusting the diameter of the aperture 4, whereby the focal depth is changed. Another characteristic of the secondary electron image is that, when observed at the same illumination angle, the focal depth is shallow compared with the specimen forward scattered electrons. Thus, the focus for an element in the specimen surface layer or a fine structure on the order of 1 nm that exists in the specimen surface layer is adjusted based on a secondary electron magnified image.

Figure 14:
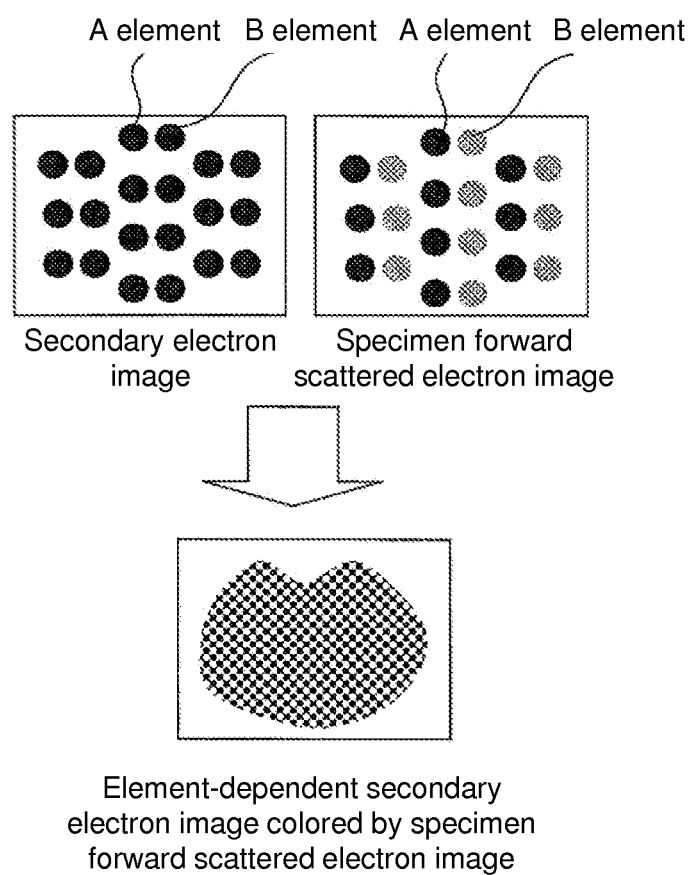
FIG. 14 shows the secondary electron image and the specimen forward scattered electron image of the specimen image including the two kinds of elements A and B observed at the magnification ratio of atomic resolution, and a diagram illustrating an example in which the atoms of the secondary electron atomic image is discriminated by the specimen forward scattered electron and colored.

FIG. 14 shows a secondary electron image and a specimen forward scattered electron image of a specimen image of the two kinds of elements A and B observed at a magnification ratio of atomic resolution, and a diagram illustrating an example of the present invention in which the atoms in the secondary electron atomic image are discriminated by the specimen forward scattered electrons and colored. The secondary electron image and the simultaneously acquired forward scattered electron image are composed by a signal mixer. The signal mixer sees the same atoms in the electron images, so that the signal mixer can adjust the mutual positions of the images with reference to the same atoms.

For comparison of contrast and the atomic number, the constituent elements in the specimen and the contrast are associated on a one-to-one basis by an image processor. The secondary electron image is colored by using the contrast of the forward scattered electron image, whereby an element-dependent secondary electron image is formed.

According to the present example, a scanning transmission electron microscope that can clarify the constituent elements in a specimen while clarifying the three-dimensional structure of the specimen can be provided.

REFERENCE SIGNS LIST 1 electron gun
2 primary electron beam
3 condenser lens system
4 aperture
5 aberration corrector
6 electron beam scanning unit
7 objective lens
8 upper secondary electron detector
9 lower secondary electron detector
10 specimen stage motion mechanism
11 projection lens
12 forward scattered electron detector
13 transmission electron detector
14 secondary electron
15 specimen
16 focusing unit
17 scanning signal generator
18 signal mixer
19 signal synchronizer
20 image processor
21 image recording unit
22 image display unit
23 taper structure specimen
24 first condenser lens
25 second condenser lens
26 third condenser lens
27 aperture
28 forward scattered electron
29 transmission electron
30 focus series of specimen scanning image
31 specimen reconstruction image

The invention claimed is:

1. A scanning transmission electron microscope comprising:
   a spherical aberration corrector for correcting a spherical aberration of an objective lens;
   a secondary electron detector;
   a condenser lens that determines an electron beam illumination angle; and
   a focusing unit,
   wherein a plurality of two-dimensional magnified scanning images of a specimen obtained by the secondary electron detector and having an atomic resolution is recorded, and a structure of a specimen uppermost surface and a structure inside the specimen are both simultaneously observed by varying a focal depth by changing an excitation current for the condenser lens.

2. The scanning transmission electron microscope according to claim 1, wherein the depth of the structure inside the specimen can be measured based on an image sharpness of the two-dimensional magnified scanning images of the specimen.

3. The scanning transmission electron microscope according to claim 1, wherein the focal depth can be changed based on a combination of excitation currents for the condenser lens without changing a probe size of the electron beam.

4. The scanning transmission electron microscope according to claim 1, wherein the specimen has a tapered structure.

5. A scanning transmission electron microscope comprising:
   a spherical aberration corrector for correcting a spherical aberration of an objective lens;
   a secondary electron detector;
   an aperture that determines an electron beam illumination angle; and
   a focusing unit,
   wherein a plurality of two-dimensional magnified scanning images of a specimen obtained by the secondary electron detector and having an atomic resolution is recorded, and a structure of a specimen uppermost surface and a structure inside the specimen are both simultaneously observed by changing a focal depth by varying the size of the aperture.

6. The scanning transmission electron microscope according to claim 5, wherein the depth of the structure inside the specimen can be measured based on an image sharpness of the two-dimensional magnified scanning images of the specimen.

7. The scanning transmission electron microscope according to claim 5, wherein the focal depth can be changed by changing the aperture size without changing a probe size of the electron beam.

8. The scanning transmission electron microscope according to claim 5, wherein the specimen has a tapered structure.

9. A scanning transmission electron microscope comprising:
   a spherical aberration corrector for correcting a spherical aberration of an objective lens;
   a secondary electron detector;
   a condenser lens that determines an electron beam illumination angle; and
   a focusing unit,
   wherein a plurality of two-dimensional magnified scanning images of a specimen obtained by the secondary electron detector and having an atomic resolution is recorded, a structure of a specimen uppermost surface and a structure inside the specimen can be both simultaneously observed by changing a focal depth by changing an excitation current for the condenser lens, the depth of the structure existing inside the specimen is measured by defocusing an electron beam with which the specimen is irradiated, and an optimum focal depth is determined.

10. The scanning transmission electron microscope according to claim 9, wherein an image sharpness is determined on a pixel unit basis, the depth of the structure existing inside the specimen is measured, the optimum focal depth is determined, and the depth of the structure inside the specimen is measured.

11. The scanning transmission electron microscope according to claim 10, wherein the depth of the structure inside the specimen is measured, and a pixel-by-pixel image sharpness evaluation result is acquired in association with a two-dimensional image.

12. The scanning transmission electron microscope according to claim 10, wherein a pixel-by-pixel image sharpness evaluation result is provided in a two-dimensional image, and a table for setting the pixel-by-pixel optimum focal depth and the electron beam illumination angle, and the condenser lens current is provided.

\* \* \* \* \*

UNITED STATES PATENT AND TRADEMARK OFFICE
CERTIFICATE OF CORRECTION

PATENT NO. : 8,878,130 B2  
APPLICATION NO. : 14/232526  
DATED : November 4, 2014  
INVENTOR(S) : Hiromi Inada et al.

Page 1 of 1

It is certified that error appears in the above-identified patent and that said Letters Patent is hereby corrected as shown below:

Item (56) on the title page should read as follows:

(56) References Cited: 6,538,249 B1 3/2003 Takane et al.

Signed and Sealed this
Twenty-first Day of April, 2015

Michelle K. Lee
*Director of the United States Patent and Trademark Office*